(12) United States Patent
Oosake

(10) Patent No.: US 12,357,149 B2
(45) Date of Patent: Jul. 15, 2025

(54) LEARNING APPARATUS, LEARNING METHOD, PROGRAM, TRAINED MODEL, AND ENDOSCOPE SYSTEM

(71) Applicant: FUJIFILM Corporation, Tokyo (JP)

(72) Inventor: Masaaki Oosake, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 372 days.

(21) Appl. No.: 18/165,934

(22) Filed: Feb. 8, 2023

(65) Prior Publication Data
US 2023/0180999 A1 Jun. 15, 2023

Related U.S. Application Data

(63) Continuation of application No. PCT/JP2021/016004, filed on Apr. 20, 2021.

(30) Foreign Application Priority Data

Aug. 28, 2020 (JP) .................................. 2020-144568

(51) Int. Cl.
*A61B 1/00* (2006.01)
*G06N 3/08* (2023.01)

(52) U.S. Cl.
CPC ...... *A61B 1/00009* (2013.01); *A61B 1/00045* (2013.01); *G06N 3/08* (2013.01); *G06T 2207/20084* (2013.01)

(58) Field of Classification Search
CPC .......... A61B 1/00009; A61B 1/000096; A61B 1/00045; A61B 1/0638; G06N 3/04;
(Continued)

(56) References Cited

U.S. PATENT DOCUMENTS 10,629,185 B2   4/2020  Matsuda et al.
11,449,759 B2 * 9/2022  Krebs .................... G06V 10/75
(Continued)

FOREIGN PATENT DOCUMENTS

JP    2015102806    6/2015
JP    2016067780    5/2016
(Continued)

OTHER PUBLICATIONS

Yimig Yang et al., "Features Combined From Hundreds of Midlayers:Hierarchical Networks With Subnetwork Nodes," Oct. 29, 2019,IEEE Transactions on Neural Networks And Learning Systems, vol. 30, No. 11, Nov. 2,pp. 3313-3316.*
(Continued)

*Primary Examiner* — Omar S Ismail
(74) *Attorney, Agent, or Firm* — JCIPRNET

(57) ABSTRACT

There are provided a learning apparatus, a learning method, a program, a trained model, and an endoscope system that can perform efficient learning even when the learning is performed using pieces of data acquired under conditions different from each other. A learning apparatus includes a hierarchical network including a first input layer, a second input layer, a first intermediate layer, a first normalization layer, a second normalization layer, a second intermediate layer, and an output layer. A learning control unit of the learning apparatus causes first learning and second learning to be performed. In the first learning, a to-be-trained model is trained based on a first error between a first recognition result and a correct answer for first data. In the second learning, the to-be-trained model is trained based on a second error between a second recognition result and a correct answer for second data.

19 Claims, 9 Drawing Sheets

(58) Field of Classification Search
CPC .......... G06N 3/045; G06N 3/08; G06N 3/084; G06T 2207/20084; G06T 7/00
See application file for complete search history.

(56) References Cited

U.S. PATENT DOCUMENTS

| | | | |
|---|---|---|---|
| 2015/0134583 | A1 | 5/2015 | Tamatsu et al. |
| 2017/0308773 | A1 | 10/2017 | Miyazaki et al. |
| 2018/0293493 | A1* | 10/2018 | Kalamkar ............... G06N 3/063 |
| 2018/0314935 | A1* | 11/2018 | Lewis .................... G06N 3/063 |
| 2018/0322386 | A1* | 11/2018 | Sridharan ................ G06F 9/54 |
| 2018/0322606 | A1* | 11/2018 | Das ........................ G06N 3/063 |
| 2019/0034800 | A1 | 1/2019 | Shiratani |
| 2019/0130255 | A1* | 5/2019 | Yim ....................... G06N 3/045 |
| 2019/0244086 | A1 | 8/2019 | Franca-Neto |
| 2020/0104634 | A1* | 4/2020 | Akahori ............ G06F 18/24143 |
| 2020/0234411 | A1* | 7/2020 | Xu ......................... H04N 23/60 |
| 2021/0097691 | A1* | 4/2021 | Liu ....................... G06V 10/764 |
| 2021/0133473 | A1 | 5/2021 | Oosake et al. |
| 2021/0150702 | A1* | 5/2021 | Claessen ................ G06T 17/10 |
| 2021/0287430 | A1* | 9/2021 | Li ............................ G06T 7/74 |
| 2021/0393109 | A1* | 12/2021 | Iketani ............. A61B 1/000094 |
| 2022/0044406 | A1 | 2/2022 | Spizhevoy et al. |

FOREIGN PATENT DOCUMENTS

| | | |
|---|---|---|
| JP | 2017199149 | 11/2017 |
| WO | 2017158575 | 9/2017 |
| WO | 2020022027 | 1/2020 |

OTHER PUBLICATIONS

Lei Cai et al.,"A review of the application of deep learning in medical image classification and segmentation," Feb. 6, 2020,Ann Transl Med 2020;8(11):713,pp. 1-12.*

Maribel Torres-Velázquez et al.,"Application and Construction of Deep Learning Networks in Medical Imaging," Oct. 13, 2020, IEEE Transactions on Radiation And Plasma Medical Sciences, vol. 5, No. 2, Mar. 2021,pp. 137-153.*

Weipeng Cao et al.,"A review on neural networks with random weights," Sep. 6, 2017, Neurocomputing 275 (2018),pp. 278-283.*

Hyunseok Seo et al.,"Machine learning techniques for biomedical image segmentation: An overview of technical aspects and introduction to state-of-art applications," May 30, 2019, Med. Phys. 47 (5), May 2020,pp. e148-e162.*

Kaiyuan Jiang et al.,"Network Intrusion Detection Combined Hybrid Sampling With Deep Hierarchical Network," Feb. 24, 2020,IEEE Access, vol. 8,2020,pp. 32464-32470.*

Ajay Shrestha et al.,"Review of Deep Learning Algorithms and Architectures," May 1, 2019, IEEE Access ,vol. 7,2019,pp. 53040-53060.*

Maayan Frid-Adar et al.,"GAN-based synthetic medical image augmentation for increased CNN performance in liver lesion classification," Sep. 21, 2018,Neurocomputing 321 (2018),pp. 321-326.*

"Office Action of Co-pending U.S. Appl. No. 17/148,514", issued on Aug. 17, 2023, pp. 1-30.

"Notice of Reasons for Refusal of Japan Co-pending Application No. 2020-532265", issued on Nov. 19, 2021, with English translation thereof, p. 1-p. 8.

Ito, Hayato et al., "Classification of neoplasia and non-neoplasia for colon endocytoscopic images by convolutional neural network", IEICE Technical Report, Sep. 2017, submit with English abstract, pp. 1-7.

"International Search Report (Form PCT/ISA/210) of PCT/JP2019/026688," mailed on Oct. 1, 2019, with English translation thereof, pp. 1-5.

"Written Opinion of the International Searching Authority (Form PCT/ISA/237) of PCT/JP2019/026688," mailed on Oct. 1, 2019, with English translation thereof, pp. 1-10.

"Office Action of U.S. Related Application, U.S. Appl. No. 17/148,514", issued on Jan. 4, 2024, p. 1-p. 27.

"Notice of allowance of U.S. Related Application, U.S. Appl. No. 17/148,514", issued on Jun. 14, 2024, p. 1-p. 10.

"Office Action of Japan Counterpart Application", issued on Jun. 14, 2024, with English translation thereof, p. 1-p. 8.

Sergey Ioffe et al., "Batch Normalization: Accelerating Deep Network Training by Reducing Internal Covariate Shift", Cornell University, arXiv:1502.03167v3, Mar. 2015, pp. 1-11.

"International Search Report (Form PCT/ISA/210) of PCT/JP2021/016004," mailed on Jul. 20, 2021, with English translation thereof, pp. 1-5.

"Written Opinion of the International Searching Authority (Form PCT/ISA/237) of PCT/JP2021/016004," mailed on Jul. 20, 2021, with English translation thereof, pp. 1-8.

* cited by examiner

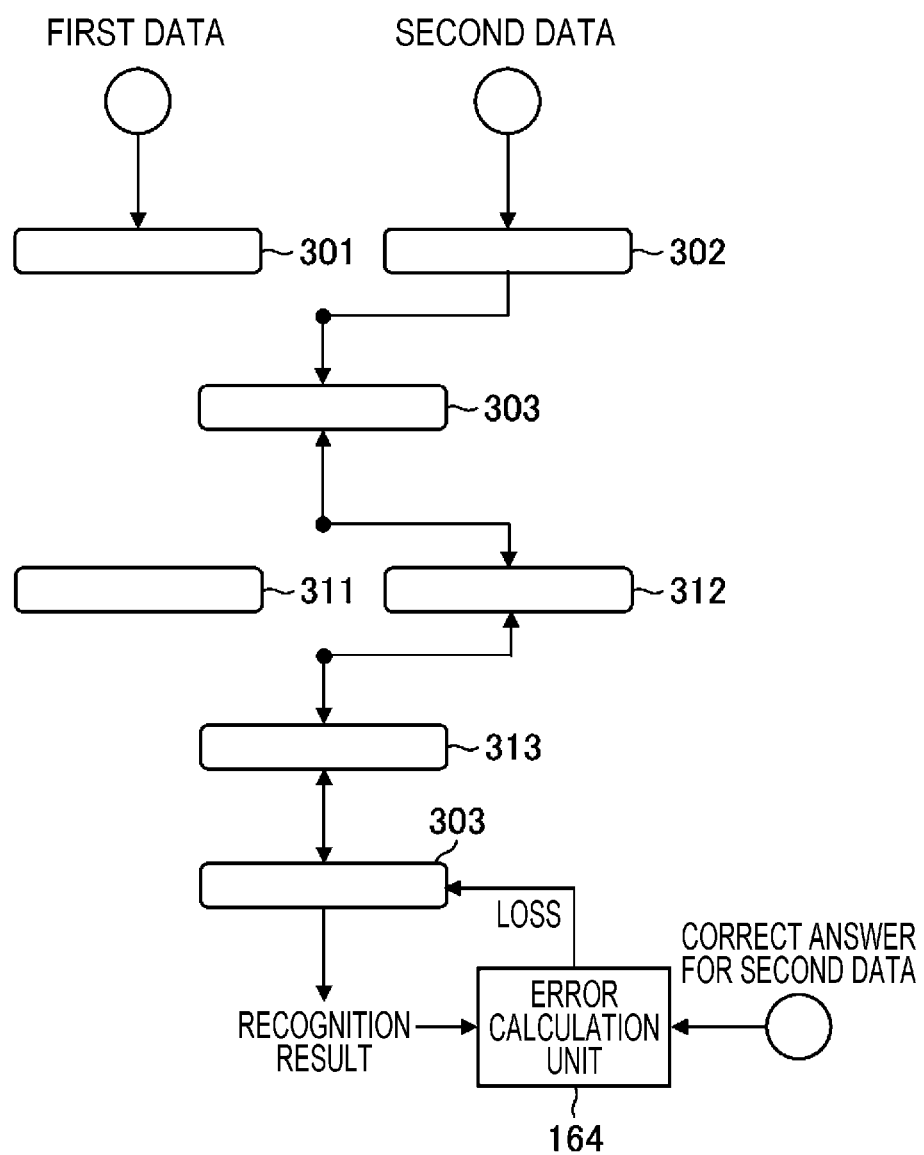

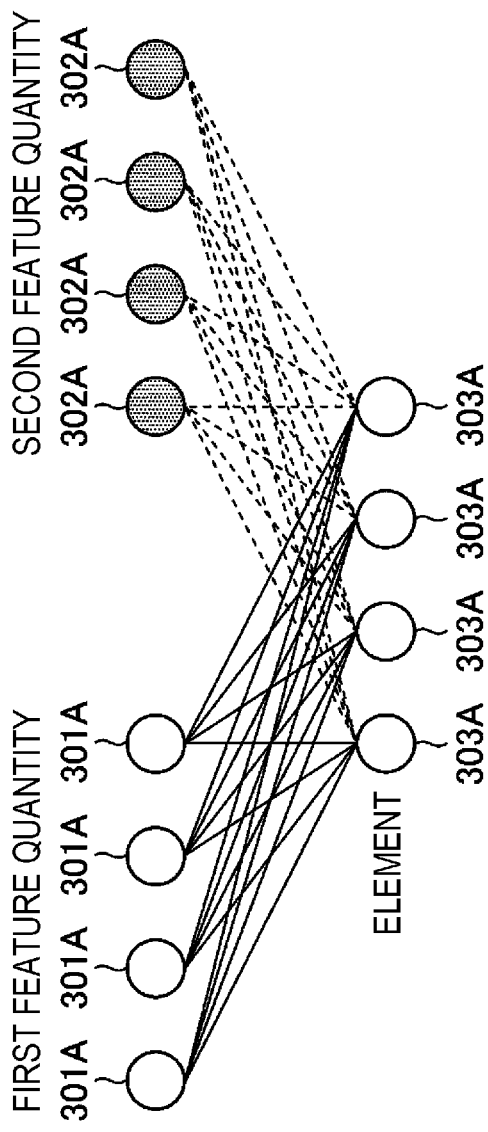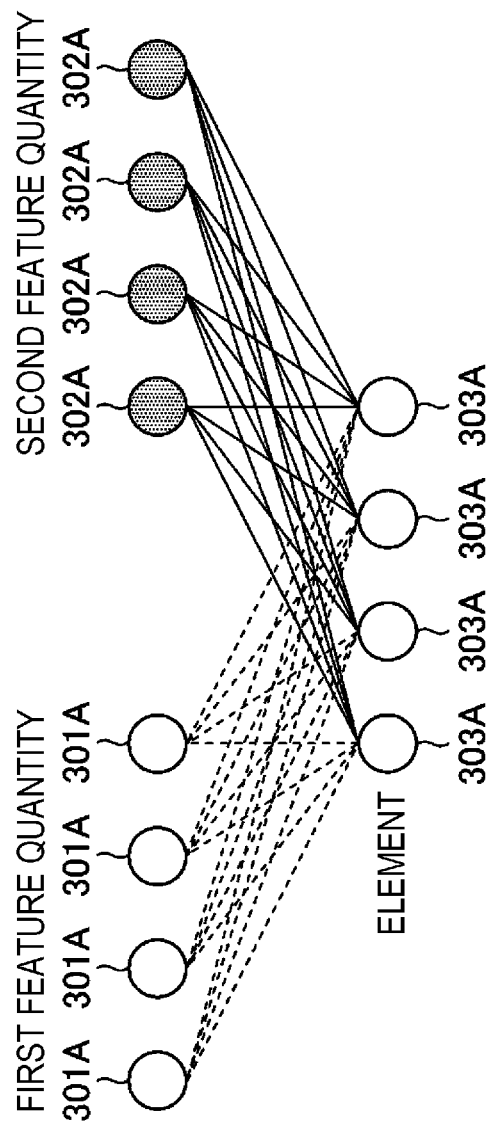

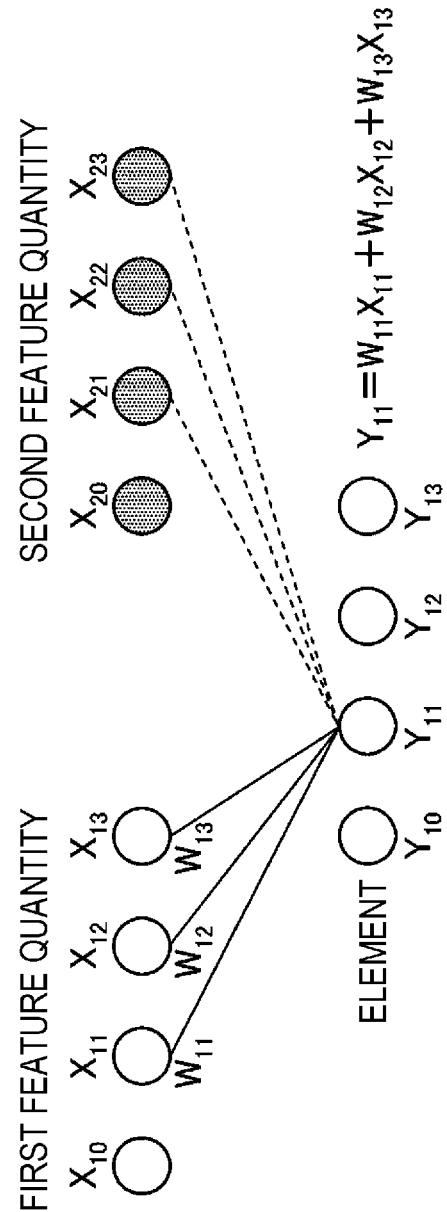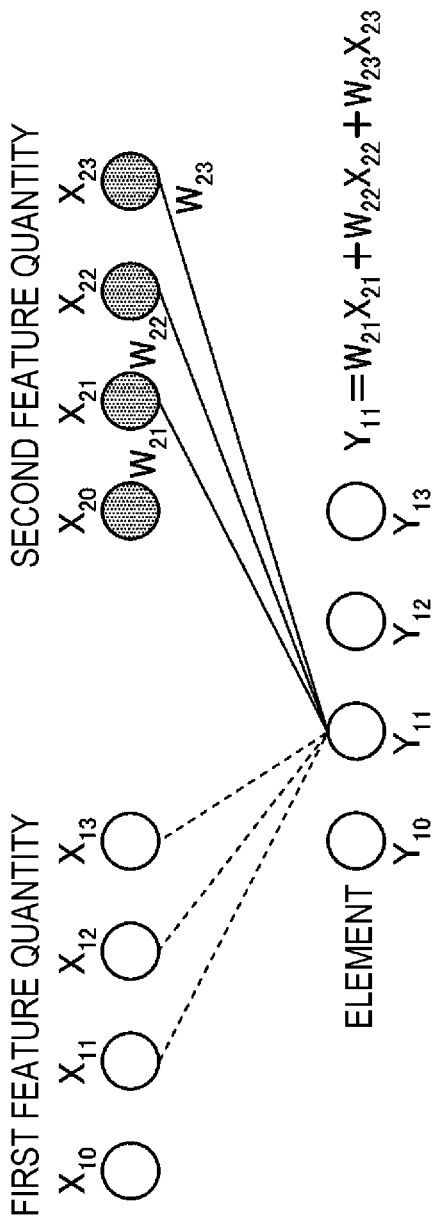

LEARNING APPARATUS, LEARNING METHOD, PROGRAM, TRAINED MODEL, AND ENDOSCOPE SYSTEM

CROSS-REFERENCE TO RELATED APPLICATIONS

The present application is a Continuation of PCT International Application No. PCT/JP2021/016004 filed on Apr. 20, 2021 claiming priority under 35 U.S.0 § 119(a) to Japanese Patent Application No. 2020-144568 filed on Aug. 28, 2020. Each of the above applications is hereby expressly incorporated by reference, in its entirety, into the present application.

BACKGROUND OF THE INVENTION

1. Field of the Invention

The present invention relates to a learning apparatus, a learning method, a program, a trained model, and an endoscope system, and more particularly to a learning apparatus, a learning method, a program, a trained model, and an endoscope system that perform learning using a hierarchical network.

2. Description of the Related Art

In the field of machine learning, it is known that learning is performed using a hierarchical network. A hierarchical network is generally constituted by a plurality of layers that perform feature extraction, recognition, and so on. There are various types in terms of specific network configurations and learning methods.

For example, WP2020/022027A describes a learning apparatus for the purpose of appropriately learning a first data group and a second data group that are acquired under conditions different from each other. Specifically, WO2020/022027A describes a hierarchical network in which the first data group and the second data group acquired under the conditions different from each other are respectively input to a first input layer and a second input layer that are independent of each other and an intermediate layer common to the first input layer and the second input layer is provided.

In order to advance machine learning, there is known a technique of normalizing a calculated feature quantity to improve the accuracy of a recognizer, as described in Sergey Ioffe, Christian Szegedy, "Batch Normalization: Accelerating Deep Network Training by Reducing Internal Covariate Shift", [online], Mar. 2, 2015, Cornell University, arXiv: 1502.03167v3[cs.LG], (searched on Aug. 17, 2020), Internet <URL: https://arxiv. org/abs/1502.03167>.

SUMMARY OF THE INVENTION

However, there is an issue that normalization such as the technique described in Sergey Ioffe, Christian Szegedy, "Batch Normalization: Accelerating Deep Network Training by Reducing Internal Covariate Shift", [online], Mar. 2, 2015, Cornell University, arXiv:1502.03167v3[cs.LG], (searched on Aug. 17, 2020), Internet <URL: https://arxiv.org/abs/1502.03167> is not appropriately applicable to each of feature quantities respectively obtained with a first data group and a second data group acquired under conditions different from each other as in the hierarchical network described in WO2020/022027A above. When performing normalization on feature quantities, different normalization is supposed to be performed in units of a data group acquired under the same condition. However, since the hierarchical network described in Wo2020/022027A has a configuration in which the intermediate layer is provided in common, normalization cannot be performed on a feature quantity output from the intermediate layer under different conditions for different pieces of input data. Thus, efficient learning may not be performed.

The present invention is made in view of such a circumstance, and an object thereof is to provide a learning apparatus, a learning method, a program, a trained model, and an endoscope system that can perform efficient learning even when the learning is performed using pieces of data acquired under conditions different from each other.

To this end, a learning apparatus according to one aspect of the present invention is a learning apparatus including a processor configured to implement a to-be-trained model of a recognizer and a learning control unit that trains the to-be-trained model. The to-be-trained model includes a hierarchical network including a first input layer, a second input layer, a first intermediate layer, a first normalization layer, a second normalization layer, a second intermediate layer, and an output layer. The first input layer receives first data and outputs a first feature quantity. The first data is data selected from a first data group constituted by a plurality of pieces of data acquired under a first condition. The second input layer is independent of the first input layer, and receives second data and outputs a second feature quantity. The second data is data selected from a second data group constituted by a plurality of pieces of data that belong to a category identical to a category of the pieces of data constituting the first data group and that are acquired under a second condition different from the first condition. The first intermediate layer is an intermediate layer common to the first input layer and the second input layer, and outputs a first intermediate feature quantity in response to receiving the first feature quantity and outputs a second intermediate feature quantity in response to receiving the second feature quantity. The first normalization layer receives the first intermediate feature quantity and outputs a first normalized feature quantity based on the first intermediate feature quantity. The second normalization layer receives the second intermediate feature quantity and outputs a second normalized feature quantity based on the second intermediate feature quantity. The second intermediate layer is an intermediate layer common to the first normalization layer and the second normalization layer, and outputs a third intermediate feature quantity in response to receiving the first normalized feature quantity and outputs a fourth intermediate feature quantity in response to receiving the second normalized feature quantity. The output layer receives the third intermediate feature quantity or the fourth intermediate feature quantity and outputs a first recognition result based on the third intermediate feature quantity in response to receiving the third intermediate feature quantity and outputs a second recognition result based on the fourth intermediate feature quantity in response to receiving the fourth intermediate feature quantity. The learning control unit causes first learning and second learning to be performed. The first learning is learning in which the to-be-trained model is trained based on a first error between the first recognition result and a correct answer for the first data. The second learning is learning in which the to-be-trained model is trained based on a second error between the second recognition result and a correct answer for the second data.

In this aspect, the first intermediate layer outputs the first intermediate feature quantity in response to receiving the first feature quantity based on the first data, and outputs the second intermediate feature quantity in response to receiving the second feature quantity based on the second data. The first normalization layer receives the first intermediate feature quantity and outputs the first normalized feature quantity. The second normalization layer receives the second intermediate feature quantity and outputs the second normalized feature quantity. The second intermediate layer receives the first normalized feature quantity and the second normalized feature quantity. Thus, in this aspect, since the first intermediate feature quantity derived from the first data and the second intermediate feature quantity derived from the second data can be normalized under different conditions, the first intermediate feature quantity and the second intermediate feature quantity can be appropriately normalized. Consequently, efficient learning can be performed.

In this aspect, the first data and the second data are respectively input to the first input layer and the second input layer that are independent of each other. The first input layer and the second input layer separately calculate the respective feature quantities. Thus, the feature quantity calculation in one of the first and second input layers is not affected by the feature quantity calculation in the other input layer. In this aspect, in addition to feature extraction in the input layers (the first input layer and the second input layer), the first intermediate feature quantity and the second intermediate feature quantity are further calculated in the first intermediate layer common to the first input layer and the second input layer. Thus, the feature quantity calculated from the first data or the second data in the input layer can be reflected in calculation of the intermediate feature quantity in the first intermediate layer. The second intermediate layer is also common to the first normalization layer and the second normalization layer. Thus, the first normalized feature quantity and the second normalized feature quantity can be similarly reflected in calculation of the intermediate feature quantity in the second intermediate layer. In addition, since a hierarchical network involves many parameters, overlearning is likely to occur. However, overlearning can be avoided by providing a large amount of data. In the learning apparatus according to this aspect, learning can be performed in the intermediate layer using a large amount of data including both the first data and the second data. Thus, overlearning is unlikely to occur. On the other hand, since the input layer is configured as the first input layer and the second input layer which are independent of each other, the number of parameters of each input layer reduces. Thus, overlearning is unlikely to occur even with a small amount of data. According to this aspect, pieces of data that belong to the identical category but are acquired under different conditions can be appropriately learned in this manner.

In the this aspect and each aspect below, as for "the first feature quantity based on the feature quantity output from the first input layer and the second feature quantity based on the feature quantity output from the second input layer", the feature quantity output from the first input layer and the feature quantity output from the second input layer may be respectively input as the first feature quantity and the second feature quantity without any processing. Alternatively, a feature quantity obtained by performing some kind of processing on the feature quantity output from the first input layer and a feature quantity obtained by performing some kind of processing on the feature quantity output from the second input layer may be respectively input as the first feature quantity and the second feature quantity. In addition, "belonging to the identical category" indicates a combination of an image and an image, text and text, or sound and sound. "The first condition and the second condition being different" excludes "dividing pieces of data acquired under the same condition into two".

In this aspect and each aspect below, each of the first input layer, the second input layer, and the intermediate layer may be constituted by a single layer or by a plurality of layers. In addition, the number of layers constituting the first input layer and the number of layers constituting the second input layer may be the same or different. The hierarchical network may include an output layer, a recognition layer, or the like in addition to the first input layer, the second input layer, and the intermediate layer.

In addition, in this aspect and each aspect below, the number of layers of the first input layer, the number of layers of the second input layer, and parameters in each layer are preferably adjusted in consideration of a result of learning (for example, an error or loss between a recognition result and correct answer data, or the like) so that the feature quantity output from the first input layer and the feature quantity output from the second input layer can appropriately express features of the first data and the second data, respectively. Further, as for the intermediate layer, the number of layers of the intermediate layer and the parameters in each layer are preferably adjusted similarly in consideration of the result of learning.

Preferably, the learning control unit causes the first learning to be performed at least twice, and the second intermediate layer outputs the fourth intermediate feature quantity in the second learning in a period after the third intermediate feature quantity in the preceding first learning is output and before the third intermediate feature quantity in the following first learning is output.

In a case where the first learning is consecutively performed multiple times and then the second learning is performed, the feature quantity calculated in the intermediate layer may be strongly affected by the first data and learning (calculation of the feature quantity) is possibly not appropriately performed for the second data (the same applies to the opposite case). Therefore, in this aspect, the fourth intermediate feature quantity is calculated in the period after calculation of the third intermediate feature quantity ends and before another calculation of third intermediate feature quantity is started. Consequently, a circumstance in which the feature quantity calculated in calculation of the fourth intermediate feature quantity is excessively affected by the first data is avoided, and learning can be appropriately performed for the first data and the second data.

Preferably, the learning control unit causes the first learning to be performed at least twice, and the second intermediate layer outputs the fourth intermediate feature quantity in the second learning after output of the third intermediate feature quantity in the preceding first learning and output of the third intermediate feature quantity in the following first learning are completed.

In this aspect, similarly to the case described above, a circumstance in which the feature quantity calculated in calculation of the fourth intermediate feature quantity is excessively affected by the first data is avoided, and learning can be appropriately performed for the first data and the second data.

Preferably, the hierarchical network is a convolutional neural network.

Preferably, the first normalization layer calculates the first normalized feature quantity through a batch normalization process, and the second normalization layer calculates the second normalized feature quantity through a batch normalization process.

Preferably, the first input layer outputs the first feature quantity through an operation including any one of a convolutional operation, a pooling process, a batch normalization process, or an activation process.

Preferably, the second input layer outputs the second feature quantity through an operation including any one of a convolutional operation, a pooling process, a batch normalization process, or an activation process.

Preferably, the first intermediate layer outputs the first intermediate feature quantity or the second intermediate feature quantity through an operation including any one of a convolutional operation, a pooling process, or an activation process.

Preferably, the second intermediate layer outputs the third intermediate feature quantity or the fourth intermediate feature quantity through an operation including any one of a convolutional operation, a pooling process, or an activation process.

Preferably, the first input layer receives, as the first data, first image data acquired under the first condition, and the second input layer receives, as the second data, second image data acquired under the second condition different from the first condition.

Preferably, the first condition and the second condition are different from each other in at least one of an imaging device, a wavelength balance of observation light, a resolution, or image processing to be performed on an image.

Note that in this aspect, it is assumed that "being different in an imaging device" means that "modalities are the same but the models, model numbers, performances, or the like are different". For example, an endoscope apparatus and a computed tomography (CT) apparatus are different modalities. In addition, "being different in a wavelength balance of observation light" means that the wavelength ranges of the observation light and/or the relative relationship between intensities in the respective wavelength ranges of the observation light are different. In addition, "being different in image processing to be performed on an image" includes, but is not limited to, processing for emphasizing or reducing the influence of a specific wavelength component, or processing for making a specific target or region be emphasized or less conspicuous, for example.

Preferably, the first input layer receives, as the first image data, first medical image data acquired using first observation light, and the second input layer receives, as the second image data, second medical image data acquired using second observation light different from the first observation light in the wavelength balance.

"Which structure of a photographic subject is clearly (or indistinctly) depicted in a captured image" depends on the wavelength balance of the observation light used for imaging. Thus, images may be acquired using a plurality of types of observation light having different wavelength balances in a scene of diagnosis or examination. However, in this aspect, learning of images can be appropriately performed even in such a case. Note that in this aspect and each aspect below, the "medical image" is also referred to as an "image for medical use".

Preferably, the first input layer receives, as the first image data, the first medical image data acquired using white light as the first observation light, and the second input layer receives, as the second image data, the second medical image data acquired using narrow-band light as the second observation light.

When medical images are acquired, the images are often acquired using white light as the observation light to allow for visual check by a user. On the other hand, in the case of the narrow-band light, a structure, such as a detail or a deep portion of the subject, which is different from that observed with the white-light image can be observed depending on the wavelength. However, since the narrow-band light is not suitable for visual observation, the number of images acquired is smaller than the number of white-light images. In this aspect, learning can be appropriately performed even in such a case. Note that in this aspect, the "narrow-band light" may be observation light having a short wavelength such as blue light or violet light, or may be observation light having a long wavelength such as red light or infrared light.

Preferably, the first input layer receives, as the first image data, the first medical image data acquired using first narrow-band light as the first observation light, and the second input layer receives, as the second image data, the second medical image data acquired using, as the second observation light, second narrow-band light different from the first narrow-band light.

When medical images are acquired, a plurality of kinds of narrow-band light may be used as the observation light to acquire images depending on the usage of the images. According to this aspect, learning can be appropriately performed even in such a case. Note that "the second narrow-band light different from the first narrow-band light" means that the first narrow-band light and the second narrow-band light are different in the wavelength range of the observation light and/or the intensity of the observation light.

A learning method according to another aspect of the present invention is a learning method for a learning apparatus including a processor configured to implement a to-be-trained model of a recognizer and a learning control unit that trains the to-be-trained model. The to-be-trained model includes a hierarchical network including a first input layer, a second input layer, a first intermediate layer, a first normalization layer, a second normalization layer, a second intermediate layer, and an output layer. The first input layer receives first data and outputs a first feature quantity. The first data is data selected from a first data group constituted by a plurality of pieces of data acquired under a first condition. The second input layer is independent of the first input layer, and receives second data and outputs a second feature quantity. The second data is data selected from a second data group constituted by a plurality of pieces of data that belong to a category identical to a category of the pieces of data constituting the first data group and that are acquired under a second condition different from the first condition. The first intermediate layer is an intermediate layer common to the first input layer and the second input layer, and outputs a first intermediate feature quantity in response to receiving the first feature quantity and outputs a second intermediate feature quantity in response to receiving the second feature quantity. The first normalization layer receives the first intermediate feature quantity and outputs a first normalized feature quantity based on the first intermediate feature quantity. The second normalization layer receives the second intermediate feature quantity and outputs a second normalized feature quantity based on the second intermediate feature quantity. The second intermediate layer is an intermediate layer common to the first normalization layer and the second normalization layer, and outputs a third intermediate feature quantity in response to receiving the first normalized feature quantity and outputs a fourth intermediate feature quantity in response to receiving the second normalized feature quantity. The output layer receives the third intermediate feature quantity or the fourth intermediate feature quantity and outputs a first recognition result based on the third intermediate feature quantity in response to receiving the third intermediate feature quantity and outputs a second recognition result based on the fourth intermediate feature quantity in response to receiving the fourth intermediate feature quantity. The learning method includes a first learning step of training, with the learning control unit, the to-be-trained model on the basis of a first error between the first recognition result and a correct answer for the first data; and a second learning step of training, with the learning control unit, the to-be-trained model on the basis of a second error between the second recognition result and a correct answer for the second data.

A program according to another aspect of the present invention is a program causing a learning method for a learning apparatus to be executed, the learning apparatus including a processor configured to implement a to-be-trained model of a recognizer and a learning control unit that trains the to-be-trained model. The to-be-trained model includes a hierarchical network including a first input layer, a second input layer, a first intermediate layer, a first normalization layer, a second normalization layer, a second intermediate layer, and an output layer. The first input layer receives first data and outputs a first feature quantity. The first data is data selected from a first data group constituted by a plurality of pieces of data acquired under a first condition. The second input layer is independent of the first input layer, and receives second data and outputs a second feature quantity. The second data is data selected from a second data group constituted by a plurality of pieces of data that belong to a category identical to a category of the pieces of data constituting the first data group and that are acquired under a second condition different from the first condition. The first intermediate layer is an intermediate layer common to the first input layer and the second input layer, and outputs a first intermediate feature quantity in response to receiving the first feature quantity and outputs a second intermediate feature quantity in response to receiving the second feature quantity. The first normalization layer receives the first intermediate feature quantity and outputs a first normalized feature quantity based on the first intermediate feature quantity. The second normalization layer receives the second intermediate feature quantity and outputs a second normalized feature quantity based on the second intermediate feature quantity. The second intermediate layer is an intermediate layer common to the first normalization layer and the second normalization layer, and outputs a third intermediate feature quantity in response to receiving the first normalized feature quantity and outputs a fourth intermediate feature quantity in response to receiving the second normalized feature quantity. The output layer receives the third intermediate feature quantity or the fourth intermediate feature quantity and outputs a first recognition result based on the third intermediate feature quantity in response to receiving the third intermediate feature quantity and outputs a second recognition result based on the fourth intermediate feature quantity in response to receiving the fourth intermediate feature quantity. The learning method includes a first learning step of training, with the learning control unit, the to-be-trained model on the basis of a first error between the first recognition result and a correct answer for the first data; and a second learning step of training, with the learning control unit, the to-be-trained model on the basis of a second error between the second recognition result and a correct answer for the second data.

A trained model of a recognizer according to another aspect of the present invention is obtained by the learning method described above.

An endoscope system according to another aspect of the present invention includes the trained model of the recognizer described above.

Preferably, the first condition and the second condition are different from each other in at least one of an imaging device, a wavelength balance of observation light, a resolution, or image processing to be performed on an image.

According to the present invention, efficient learning can be performed even when the learning is performed using pieces of data acquired under conditions different from each other.

BRIEF DESCRIPTION OF THE DRAWINGS

FIG. 6 is a diagram describing second learning;

FIGS. 7A and 7B are diagrams illustrating how a feature quantity to be input to a first intermediate layer is switched;

FIGS. 8A and 8B are diagrams illustrating how convolution is performed when feature quantities are input from a first input layer and a second input layer to the first intermediate layer;

DESCRIPTION OF THE PREFERRED EMBODIMENTS

A learning apparatus, a learning method, a program, a trained model, and an endoscope system according to preferred embodiments of the present invention will be described below with reference to the accompanying drawings.

Configuration of Learning Apparatus

Figure 1:
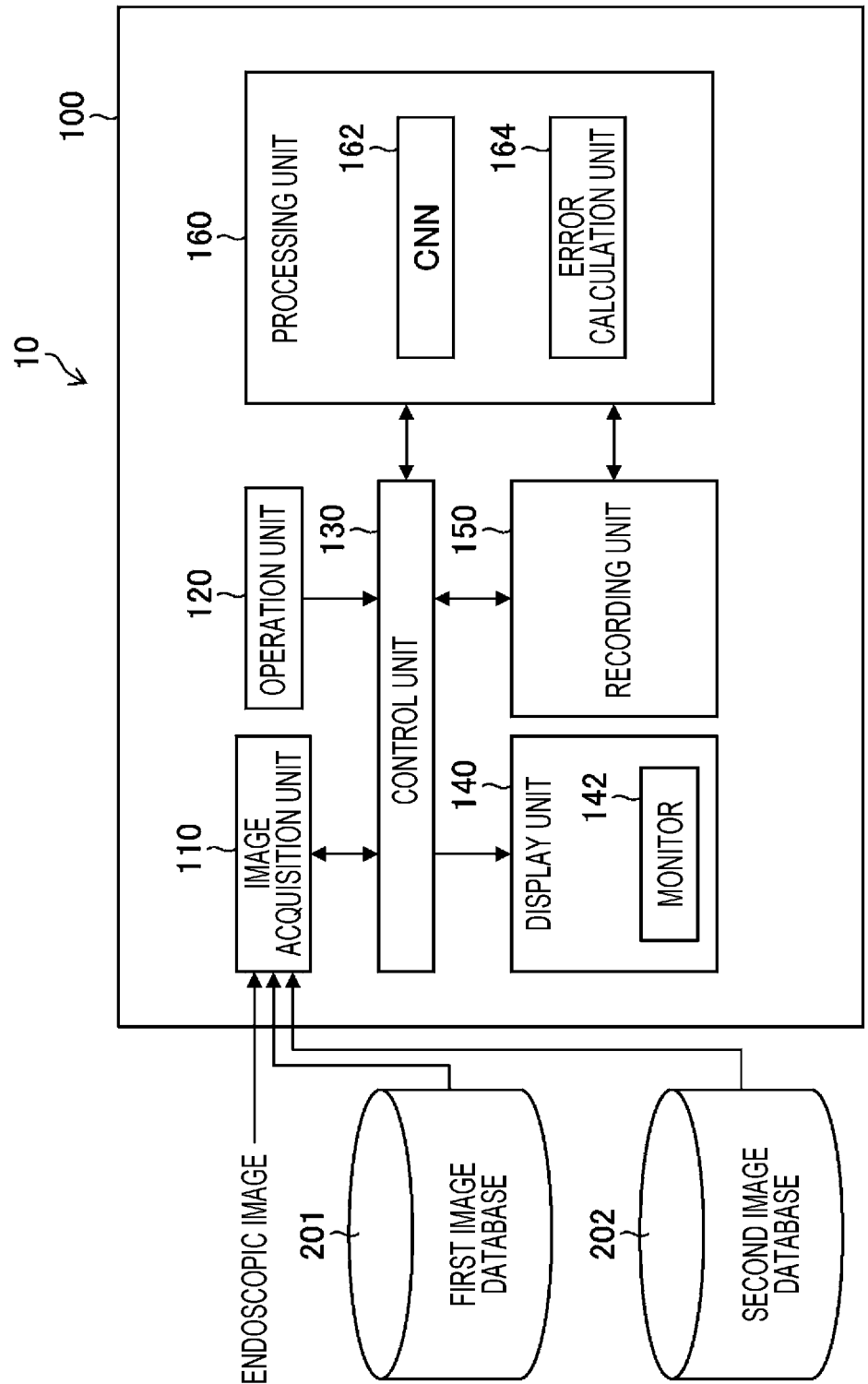
FIG. 1 is a block diagram illustrating a configuration of a learning apparatus.

FIG. 1 is a block diagram illustrating a configuration of a learning apparatus 10 according to the present embodiment. The learning apparatus 10 includes a recognizer 100 that performs a recognition process based on an image captured with an endoscope inserted into a subject, a first image database 201 that records a plurality of endoscopic images acquired using normal light (white light) as observation light, and a second image database 202 that records a plurality of endoscopic images acquired using special light (narrow-band light) as observation light. Note that in the following description, an image acquired using normal light (white light) as observation light is referred to as a "normal-light image" (or "white-light image"), and an image acquired using special light (narrow-band light) as observation light is referred to as a "special-light image" (or "narrow-band-light image"). The endoscopic images recorded in the first image database 201 and the second image database 202 are an example of medical images.

First Image Database and Second Image Database

Normal-Light Images and Special-Light Images

The first image database 201 and the second image database 202 are constituted by a recording medium such as a hard disk. In the first image database 201, a plurality of normal-light images (first data group, first data, first image data, or first medical images) captured using the normal light as the observation light (first observation light) are recorded. In the second image database 202, a plurality of special-light images (second data group, second data, second image data, or second medical images) captured using the special light as the observation light (second observation light) are recorded. That is, the plurality of normal-light images recorded in the first image database 201 are an aspect of a "plurality of pieces of data acquired under a first condition" in the present invention, and the plurality of special-light images recorded in the second image database 202 are an aspect of a "plurality of pieces of data acquired under a second condition different from the first condition" in the present invention. The special light (narrow-band light) used for capturing special-light images can be, for example, narrow-band blue light. Alternatively, the special light may be light of another wavelength such as narrow-band red light. In addition, the case where the first observation light and the second observation light are the white light and the narrow-band light, respectively, has been described in the example above. However, medical images such as endoscopic images may be used which are acquired using, as the observation light, first narrow-band light and second narrow-band light that are different from each other in a wavelength range and/or intensity.

As described above, an acquisition condition (first condition) of the normal-light images and an acquisition condition (second condition) of the special-light images are different from each other in the wavelength balance of the observation light. In addition to this, the normal-light images and the special-light images may be different from each other in an imaging device, a resolution, and image processing to be performed on the images. That is, the first condition and the second condition may be different from each other in at least one of the imaging device, the wavelength balance of the observation light, the resolution, or the image processing to be performed on an image. "Being different in the imaging device" includes, but is not limited to, using endoscopes having different optical system characteristics or different processor performances. In addition, "being different in the image processing to be performed on an image" includes, but is not limited to, the presence or absence of processing for making a specific region such as a region of interest be emphasized or less conspicuous or processing for emphasizing or reducing the influence of a specific wavelength component and/or different degrees of such processing.

Difference in Number of Pieces of Data Depending on Data Acquisition Condition

When a user performs observation or examination using an endoscope, it is often the case that the user displays an image acquired using the normal light (white light) as the observation light on a monitor to check the image. Depending on the purpose and circumstance of the observation or examination (for example, it is difficult to observe the structure of a lesion with the normal light), there may be a case where an image is acquired using the special light such as the narrow-band light as the observation light. However, the frequency with which the special light is used as the observation light is less than that of the normal light. Thus, it is often the case that the number of special-light images is significantly smaller than the number of normal-light images. When learning and/or recognition of images are performed through machine learning, learning and/or recognition needs to be performed for the special-light images. However, if the number of pieces of data of the special-light images is small, the accuracy of learning and/or recognition may decrease compared with that of the normal-light images. In view of such a circumstance, in the present embodiment, a hierarchical network configuration (described later) is adopted to enable learning and/or recognition to be appropriately performed even in a circumstance in which there is a difference between the numbers of pieces of data.

Correct Answer Data of Endoscopic Images

The first image database 201 and the second image database 202 store, in addition to endoscopic images described above, "correct answer data" for identifying a region of interest (ROI) in association with the images. Specifically, the first image database 201 stores a plurality of pieces of correct answer data each corresponding to a corresponding one of a plurality of normal-light images. The second image database 202 stores a plurality of pieces of correct answer data each corresponding to a corresponding one of a plurality of special-light images. The correct answer data is preferably a region of interest or a discrimination result designated by a doctor in an endoscopic image.

Configuration of Recognizer

The recognizer 100 includes an image acquisition unit 110, an operation unit 120, a control unit 130, a display unit 140, a recording unit 150, and a processing unit 160.

The image acquisition unit 110 is constituted by an apparatus or the like that communicates with an external server, a database, or the like via a network. The image acquisition unit 110 acquires endoscopic images and pieces of correct answer data for use in learning and recognition from the first image database 201 and the second image database 202. The image acquisition unit 110 can also acquire endoscopic images from an endoscope system, a hospital server, or the like connected to the learning apparatus 10 via a network (not illustrated).

The operation unit 120 includes input devices such as a keyboard (not illustrated) and a mouse (not illustrated). A user can perform operations necessary for processing such as image acquisition, learning, and recognition via these devices. The control unit 130 reads various programs recorded in the recording unit 150 and controls the operation of the entire learning apparatus 10 in accordance with a command input from the operation unit 120. The control unit 130 also back-propagates an error (loss) calculated by an error calculation unit 164 (described later) to a convolutional neural network (CNN) 162 to update weight parameters of the CNN 162. That is, the control unit 130 has a function of a learning control unit that causes the CNN 162 to perform learning. The CNN 162 is a learning model of the recognizer 100. After the CNN 162 performs first learning (described below) and second learning (described below), the CNN 162 becomes a trained model of the recognizer 100.

The display unit 140 includes a monitor 142 (display device). The display unit 140 displays an endoscopic image, a learning result, a recognition result, a processing condition setting screen, and so on. The recording unit 150 is constituted by a read-only memory (ROM) (not illustrated), a random access memory (RAM) (not illustrated), a hard disk (not illustrated), or the like. The recording unit 150 records therein data acquired by the image acquisition unit 110, the learning result and the recognition result obtained by the processing unit 160, and so on. The recording unit 150 also records therein programs for performing learning and recognition of endoscopic images (medical images) (which include a program for causing the learning apparatus 10 to perform a learning method of the present invention). The processing unit 160 includes the CNN 162 that is a hierarchical network, and the error calculation unit 164 that calculates a loss (error) on the basis of the output (recognition result) of the CNN 162 and the "correct answer data" described above.

Implementation of Functions with Various Processors

Functions of the image acquisition unit 110, the control unit 130, and the processing unit 160 (the CNN 162 and the error calculation unit 164) described above can be implemented using various processors. The various processors include, for example, a central processing unit (CPU) which is a general-purpose processor that executes software (program) to implement various functions. In addition, the various processors mentioned above include a graphics processing unit (GPU) which is a processor specialized for image processing and a programmable logic device (PLD) which is a processor whose circuit configuration is changeable after manufacture, such as a field programmable gate array (FPGA). Further, the various processors mentioned above include a dedicated electric circuitry which is a processor having a circuit configuration designed exclusively for executing a specific process, such as an application-specific integrated circuit (ASIC).

The function of each unit may be implemented by a single processor, or may be implemented by a plurality of processors of the same kind or of different kinds (for example, a plurality of FPGAs, a combination of a CPU and an FPGA, or a combination of a CPU and a GPU). In addition, the plurality of functions may be implemented by a single processor. Examples in which the plurality of functions are implemented by a single processor include a first configuration, as exemplified by a computer, in which a combination of one or more CPUs and software constitutes a single processor and this processor implements the plurality of functions. The examples also include a second configuration, as exemplified by a system on chip (SoC) or the like, in which a processor that implements the functions of the entire system with a single integrated circuit (IC) chip is used. As described above, the various functions are implemented using one or more of the various processors described above in terms of the hardware structure.

Further, the hardware structure of these various processors is, more specifically, electric circuitry in which circuit elements such as semiconductor elements are combined.

When the above-described processor or electric circuitry executes software (program), the processor (computer)-readable code of the software to be executed is stored in a non-transitory recording medium such as a read-only memory (ROM), and the processor refers to the software. The software stored in the non-transitory recording medium includes the program for performing the learning method according to the present invention. The code may be recorded in a non-transitory recording medium such as a magneto-optical recording apparatus of various types or a semiconductor memory, instead of the ROM. When processing using software is performed, for example, a random access memory (RAM) is used as a temporary storage area. In addition, reference can be made to data stored in, for example, an electronically erasable and programmable read-only memory (EEPROM) (not illustrated). As the ROM, the RAM, or the EEPROM, a recording medium included in the recording unit 150 can be used.

Layer Configuration of CNN

A layer configuration of the CNN 162 will be described next with reference to FIGS. 2 and 3.

Figure 2:
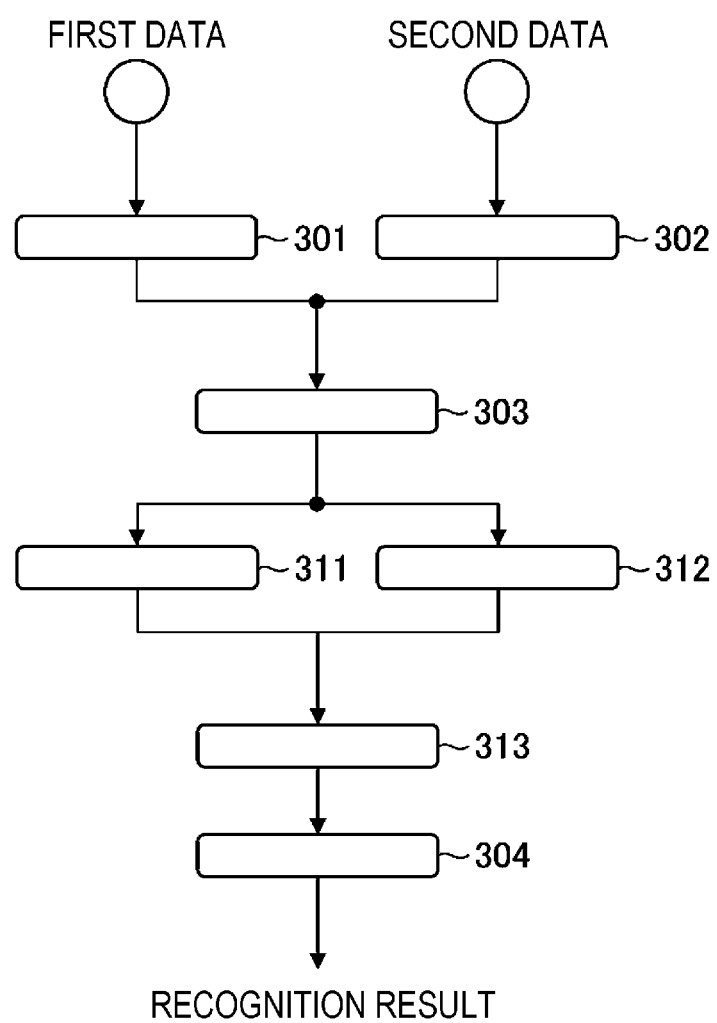
FIG. 2 is a diagram illustrating an example of a layer configuration of a convolutional neural network (CNN)
Figure 3:
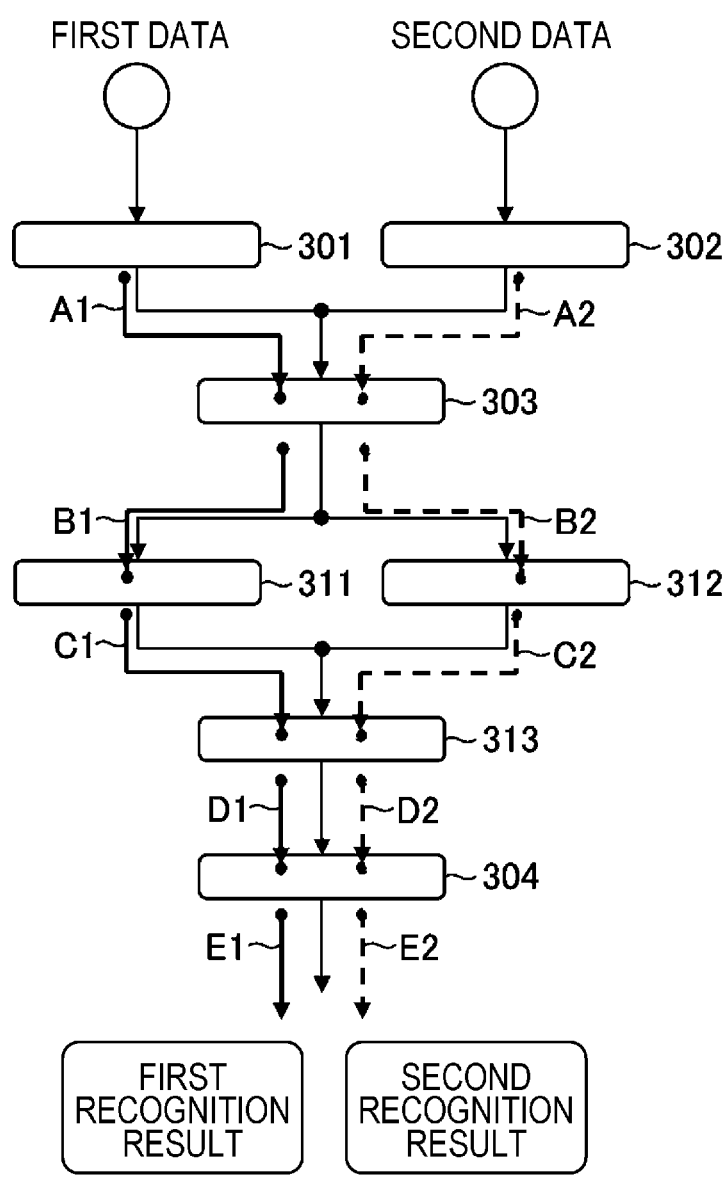
FIG. 3 is a diagram illustrating pieces of data, feature quantities, and the like that are input to and output from each layer of the CNN illustrated in FIG. 2.

FIG. 2 is a diagram illustrating an example of a layer configuration of the CNN 162. FIG. 3 is a diagram illustrating pieces of data, feature quantities, and the like that are input to and output from each layer of the CNN 162 illustrated in FIG. 2. In the examples illustrated in FIGS. 2 and 3, the CNN 162 includes a first input layer 301 (first input layer), a second input layer 302 (second input layer), a first intermediate layer 303 (intermediate layer), a first normalization layer 311 (first normalization layer), a second normalization layer 312 (second normalization layer), a second intermediate layer 313 (second intermediate layer), and an output layer 304 (output layer).

The first input layer 301 receives an image (first data) selected from the normal-light images (first data group) stored in the first image database 201 and outputs a feature quantity (first feature quantity).

The second input layer 302 is an input layer that is independent of the first input layer 301. The second input layer 302 receives an image (second data) selected from the special-light images (second data group) stored in the second image database 202 and outputs a feature quantity (second feature quantity).

The first intermediate layer 303 is an intermediate layer common to the first input layer 301 and the second input layer 302. When receiving a first feature quantity (A1) output by the first input layer 301, the first intermediate layer 303 outputs a first intermediate feature quantity (B1). When receiving the second feature quantity (A2) output by the second input layer 302, the first intermediate layer 303 outputs a second intermediate feature quantity (B2). How the feature quantities output by the first intermediate layer 303 and the second intermediate layer 313 are switched will be described later.

The first normalization layer 311 receives the first intermediate feature quantity (B1) output from the first intermediate layer 303 and outputs a first normalized feature quantity (C1) based on the first intermediate feature quantity.

The second normalization layer 312 receives the second intermediate feature quantity (B2) output from the first intermediate layer 303 and outputs a second normalized feature quantity (C2) based on the second intermediate feature quantity.

The second intermediate layer 313 is an intermediate layer common to the first normalization layer 311 and the second normalization layer 312. When receiving the first normalized feature quantity (C1) output from the first normalization layer 311, the second intermediate layer 313 outputs a third intermediate feature quantity (D1). When receiving the second normalized feature quantity (C2) output from the second normalization layer 312, the second intermediate layer 313 outputs a fourth intermediate feature quantity (D2).

The output layer 304 receives the feature quantity from the second intermediate layer 313 and outputs a recognition result of the image input to the first input layer 301 or the second input layer 302. Specifically, when receiving the third intermediate feature quantity (D1) output from the second intermediate layer 313, the output layer 304 outputs a first recognition result (E1) based on the third intermediate feature quantity (D1). When receiving the fourth intermediate feature quantity (D2) output from the second intermediate layer 313, the output layer 304 outputs a second recognition result (E2) based on the fourth intermediate feature quantity (D2). The first recognition result (E1) is a recognition result of the first data, and the second recognition result (E2) is a recognition result of the second data.

The first input layer 301, the first intermediate layer 303, the first normalization layer 311, the second intermediate layer 313, and the output layer 304 have a structure in which a plurality of "nodes" are connected to each other by "edges" and hold a plurality of weight parameters. The second input layer 302, the first intermediate layer 303, the second normalization layer 312, the second intermediate layer 313, and the output layer 304 have a structure in which a plurality of "nodes" are connected to each other by "edges" and hold a plurality of weight parameters. The values of these weight parameters change as learning progresses.

Processing performed in each layer of the CNN 162 will be described next.

Processing in Input Layers and Intermediate Layers

Each of the first input layer 301 and the second input layer 302 outputs a feature quantity through an operation including any one of a convolutional operation, a pooling process, an activation process, or a batch normalization process. Each of the first intermediate layer 303 and the second intermediate layer 313 outputs a feature quantity through an operation including any one of a convolutional operation, a pooling process, or an activation process. For example, each of the first input layer 301 and the second input layer 302, in which a convolutional operation, a pooling process, an activation process, and a batch normalization operation are combined in a layered manner, outputs a feature quantity. For example, each of the first intermediate layer 303 and the second intermediate layer 313, in which a convolutional operation, a pooling process, and an activation process are combined in a layered manner, outputs a feature quantity.

The convolutional operation is a process of acquiring a feature map through a convolutional operation using a filter onto input data (for example, an image). The convolutional operation plays a role of extracting features, such as extracting edges, from an image. Through this convolutional operation using a filter, one channel of feature map (one feature map) is generated for one filter. The size of the feature map is downscaled by convolution and reduces as the convolution is performed at each layer.

The pooling process is a process of reducing (or enlarging) the feature map output as a result of the convolutional operation to obtain a new feature map. The pooling process plays a role of providing robustness so that the extracted features are not affected by translation or the like.

In the activation process, an operation is performed on the feature map by using an activation function. The activation function to be used is a sigmoid function or a rectified linear unit (ReLU).

The batch normalization process is a process of normalizing the distribution of data in units of mini-batches used when learning is performed. The batch normalization process plays a role of making learning progress faster, reducing dependency on an initial value, suppressing overlearning, and the like.

Each of the first input layer 301, the second input layer 302, the first intermediate layer 303, and the second intermediate layer 313 can be constituted by one or a plurality of layers that perform these processes. Note that the layer configuration is not limited to a configuration including one layer for performing the convolutional operation, one layer for performing the pooling process, one layer for performing the activation process, and one layer for performing the batch normalization process, and may include a plurality layers for any of the processes.

Among these layers of the first input layer 301, the second input layer 302, the first intermediate layer 303, and the second intermediate layer 313, lower-order feature extraction (such as edge extraction) is performed in a layer adjacent to the input side and higher-order feature extraction (extraction of features related to the shape, the structure, or the like of a target) is performed as the layer approaches the output side.

Processing in Normalization Layer

The first normalization layer 311 and the second normalization layer 312 normalize a feature quantity input thereto. Specifically, the first normalization layer 311 and the second normalization layer 312 normalize a feature quantity distribution input thereto and output a normalized feature quantity. The first normalization layer 311 normalizes the first intermediate feature quantity (B1) based on the first data, whereas the second normalization layer 312 normalizes the second intermediate feature quantity (B2) based on the second data. As described above, in the CNN 162, the first normalization layer 311 dedicated to the first intermediate feature quantity (B1) and the second normalization layer 312 dedicated to the second intermediate feature quantity (B2) are independently provided. Thus, the first intermediate feature quantity (B1) and the second intermediate feature quantity (B2) are normalized under respective independent appropriate conditions. If the first intermediate feature quantity (B1) and the second intermediate feature quantity (B2) are normalized in a common normalization layer under the same conditions, the effect of the normalization process may reduce, or the normalization process may rather hinder learning of the CNN 162 from efficiently proceeding. This is because, if two feature quantities derived from the first data and the second data that are acquired under different conditions are normalized, normalization is performed to a feature quantity between the two feature quantities. Therefore, provided with the first normalization layer 311 dedicated to the first intermediate feature quantity (B1) and the second normalization layer 312 dedicated to the second intermediate feature quantity (B2) between the first intermediate layer 303 and the second intermediate layer 313, the CNN 162 implements a normalization process suitable for each of the first data and the second data. In addition, the first normalization layer 311 and the second normalization layer 312 are provided in parallel at a position between the first intermediate layer 303 and the second intermediate layer 313. Thus, the first intermediate feature quantity (B1) and the second intermediate feature quantity (B2) output from the first intermediate layer 303 can be normalized independently, and the normalized feature quantities (the first normalized feature quantity and the second normalized feature quantity) can be further output to the second intermediate layer 313. Note that the normalization process performed by the first normalization layer 311 and the second normalization layer 312 is, for example, a batch normalization process. For example, through the batch normalization process, the normalization process is performed such that the distribution of the first intermediate feature quantity (B1) has a mean of 0 and a variance of 1 and the distribution of the second intermediate feature quantity (B2) has a mean of 0 and a variance of 1. When a normal-light medical image is used as the first data and a special-light medical image is used as the second data as a specific example, the first normalization layer 311 and the second normalization layer 312 may perform normalization under different conditions in terms of color. Provided with the first normalization layer 311 and the second normalization layer 312 in this manner, the CNN 162 can appropriately perform normalization for each of the first data and the second data and can perform efficient learning even if the CNN 162 performs learning using the first data and the second data acquired under different conditions. The batch normalization process is also performed in the first input layer 301 and the second input layer 302 described above. However, since only the first data is input to the first input layer 301 and only the second data is input to the second input layer 302, the batch normalization process is dedicated to either the first data or the second data. On the other hand, since the feature quantities derived from the first data and the second data having different properties are input to the first intermediate layer 303, the first normalization layer 311 and the second normalization layer 312 are provided separately and perform normalization correctly.

Processing in Output Layer

The output layer 304 is a layer that detects the location of a region of interest depicted in an input image (normal-light image or special-light image) on the basis of the feature quantity output from the second intermediate layer 313 and outputs the result. The output layer 304 grasps the location of the region of interest depicted in the image at the pixel level in accordance with the "feature map" obtained from the second intermediate layer 313. That is, the output layer 304 can detect whether each pixel of the endoscopic image belongs to the region of interest and output the detection result.

The output layer 304 may perform discrimination of a lesion and output the discrimination result. For example, the output layer 304 may classify endoscopic images into three categories "tumorous", "non-tumorous", and "others", and may output three scores (the sum of the three scores is equal to 100%) corresponding to "tumorous", "non-tumorous", and "others" as the discrimination result. Alternatively, the output layer 304 may output the classification result when the endoscopic images can be clearly classified on the basis of the three scores. Note that when the output layer 304 outputs the discrimination result, the output layer 304 preferably includes a fully connected layer as a single last layer or fully connected layers as a plurality of last layers.

Learning Method

Figure 4:
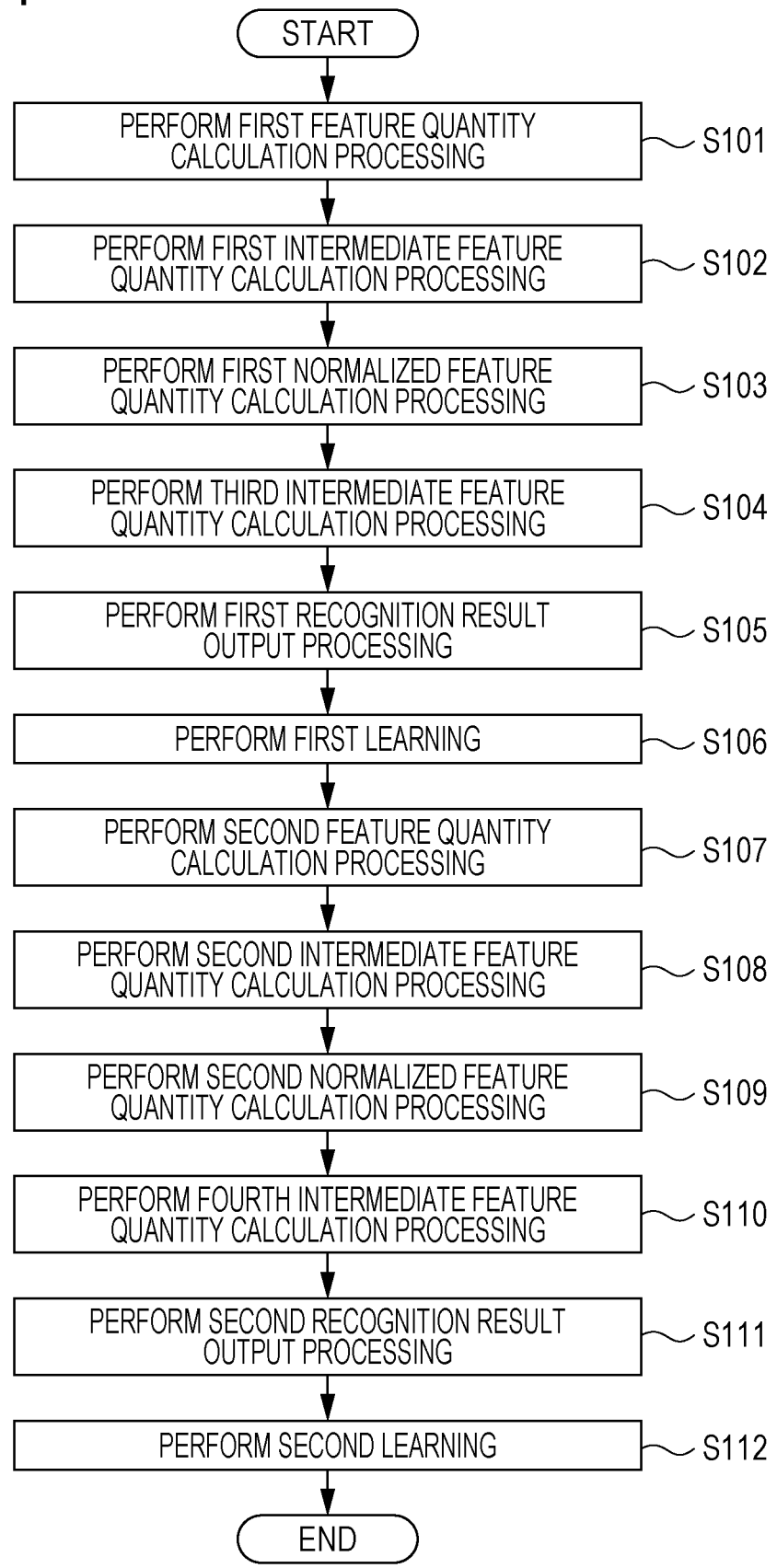
FIG. 4 is a flowchart illustrating a learning method performed by the learning apparatus.

A learning method performed by the learning apparatus 10 described above will be described next. FIG. 4 is a flowchart illustrating a learning method performed by the learning apparatus 10.

First, the control unit 130 of the learning apparatus 10 performs a first learning step (see step S106), and then performs a second learning step (see step S112).

First, the first learning will be described. The processing unit 160 performs first feature quantity calculation processing (step S101) in the first input layer 301. The processing unit 160 then performs first intermediate feature quantity calculation processing (step S102) in the first intermediate layer 303. The processing unit 160 performs first normalized feature quantity calculation processing (step S103) in the first normalization layer 311. The processing unit 160 performs third intermediate feature quantity calculation processing (step S104) in the second intermediate layer 313. The processing unit 160 performs first recognition result output processing (step S105) in the output layer 304. The control unit 130 then causes the CNN 162 to perform the first learning (step S106).

The second learning will be described next. The second learning is performed after the first learning described above. The processing unit 160 performs second feature quantity calculation processing (step S107) in the second input layer 302. The processing unit 160 then performs second intermediate feature quantity calculation processing (step S108) in the first intermediate layer 303. The processing unit 160 then performs second normalized feature quantity calculation processing (step S109) in the second normalization layer 312. The processing unit 160 then performs fourth intermediate feature quantity calculation processing (step S110) in the second intermediate layer 313. The processing unit 160 then performs second recognition result output processing (step S111) in the output layer 304. The control unit 130 then causes the CNN 162 to perform the second learning (step S112).

Each processing in the first learning and the second learning will be described in detail next.

First Learning

Figure 5:
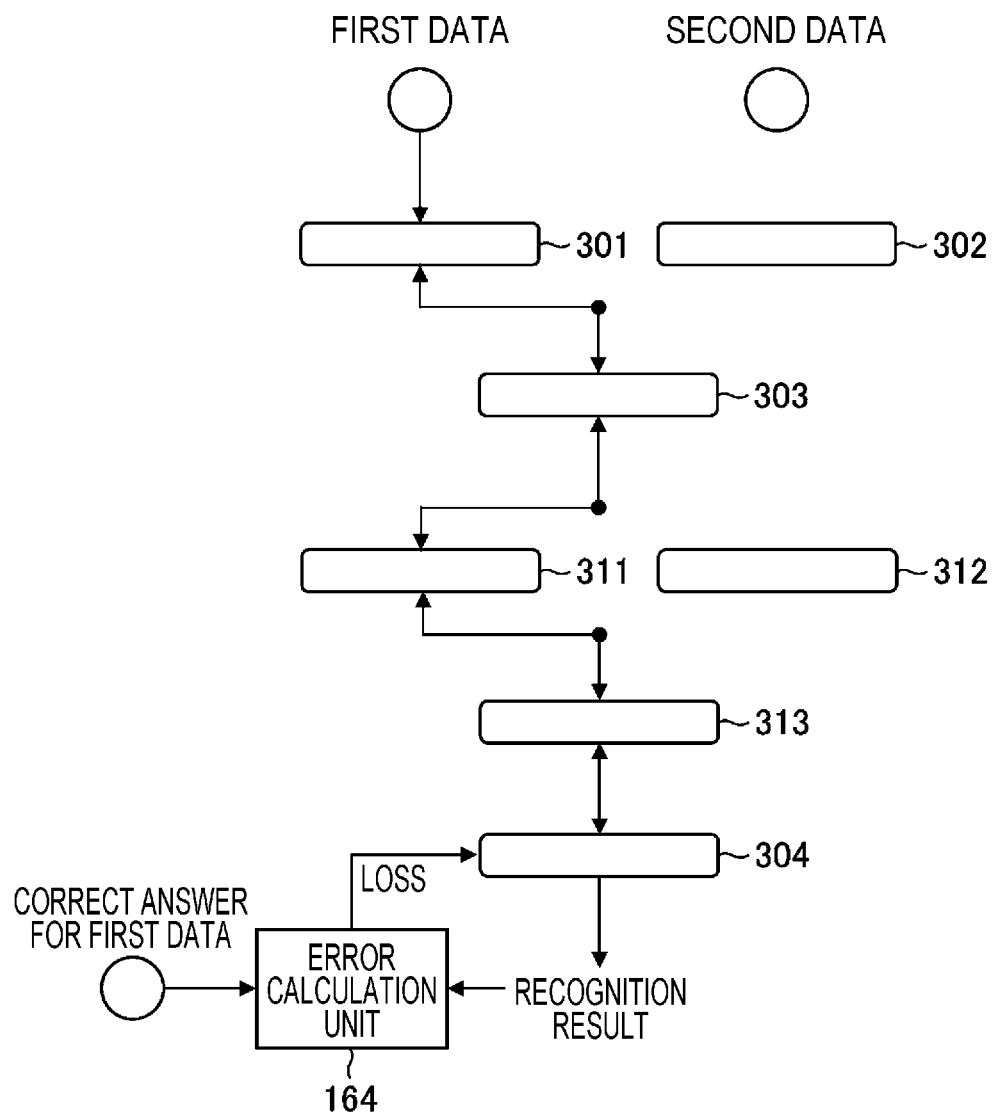
FIG. 5 is a diagram describing first learning.

FIG. 5 is a diagram describing the first learning in the CNN 162. In FIG. 5, a downward arrow indicates that information is transmitted in a direction (learning direction) from the first input layer 301 to the output layer 304 via the first intermediate layers 303, the first normalization layer 311, and the second intermediate layer 313. An upward arrow opposite to the learning direction indicates that information is transmitted from the output layer 304 to the first input layer 301 via the second intermediate layers 313, the first normalization layer 311, and the first intermediate layer 303 (error backpropagation described later).

First Feature Quantity Calculation Processing

In the first learning, a mini-batch is formed by a plurality of images (first data) selected from the plurality of normal-light images recorded in the first image database 201, and the mini-batch is input to the first input layer 301. The first input layer 301 performs the first feature quantity calculation processing (step S101) to calculate the first feature quantity.

First Intermediate Feature Quantity Calculation Processing

Since the first input layer 301 and the second input layer 302 are connected to the first intermediate layer 303 as described above, the output of the first input layer 301 and the output of the second input layer 302 are input in a switching manner when learning is performed. As illustrated in FIG. 5, when the first feature quantity output from the first input layer 301 is input to the first intermediate layer 303, the first intermediate layer 303 calculates the first intermediate feature quantity (step S102).

FIGS. 7A and 7B are diagrams illustrating how a feature quantity to be input to the first intermediate layer 303 is switched. FIG. 7A illustrates a state in which the first feature quantity is input to the first intermediate layer 303 (outputs from nodes 301A constituting layers included in the first input layer 301 are input to nodes 303A constituting the first intermediate layer 303). At the time of input, the feature quantity output from the first input layer 301 may be input, as the first feature quantity, to the first intermediate layer 303 without any processing, or a feature quantity appropriately multiplexed by a weight may be input, as the first feature quantity, to the first intermediate layer 303 (see FIG. 8A). Note that a solid line in FIGS. 7A and 7B indicates a state in which data is output or input from a node as a result of output switching described above, and a dotted line in FIGS. 7A and 7B indicates a state in which data is not output or input from a node. The nodes 301A and 303A are conceptually illustrated, and the numbers thereof are not particularly limited. These points also apply to FIGS. 8A and 8B.

FIGS. 8A and 8B are diagrams illustrating how convolution is performed when feature quantities are input from the first input layer 301 and the second input layer 302 to the first intermediate layer 303. FIG. 8A illustrates a state in which outputs of nodes $X_{11}$, $X_{12}$, and $X_{13}$ of the first input layer 301 are respectively multiplied by weight parameters $W_{11}$, $W_{12}$, and $W_{13}$ and the results are input to a node $Y_{11}$ of the first intermediate layer 303 (in the state illustrated in FIG. 8A, the output is not input to the node $Y_{11}$ from a node $X_{10}$). FIG. 8A illustrates the input relationships between the nodes $X_{11}$, $X_{12}$, and $X_{13}$ and the node $Y_{11}$. The similar relationships are established also for other nodes $Y_{10}$, $Y_{12}$, and $Y_{13}$ of the first intermediate layer 303.

First Normalized Feature Quantity Calculation Processing

The processing unit 160 performs the first normalized feature quantity calculation processing in the first normalization layer 311. Specifically, the processing unit 160 calculates the first normalized feature quantity on the basis of the first intermediate feature quantity output from the first intermediate layer 303 (step S103).

Third Intermediate Feature Quantity Calculation Processing

The processing unit 160 performs the third intermediate feature quantity calculation processing in the second intermediate layer 313 (step S104). Specifically, the processing unit 160 calculates the third intermediate feature quantity on the basis of the first normalized feature quantity output from the first normalization layer 311. Similarly to the first intermediate feature quantity calculation processing described above, the second intermediate layer 313 receives the first normalized feature quantity output from the first normalization layer 311 and the second normalized feature quantity output from the second normalization layer 312 in a switching manner. Detailed description of the third intermediate feature quantity calculation processing is omitted since the third intermediate feature quantity calculation processing is similar to the first intermediate feature quantity calculation processing.

First Recognition Result Output Processing

The output layer 304 receives the third intermediate feature quantity calculated by the second intermediate layer 313, performs the first recognition result output processing, and outputs the first recognition result (step S105).

First Learning Processing (Update of Weight Parameters through Error Backpropagation)

The error calculation unit 164 compares the first recognition result output by the output layer 304 with the correct answer for the first data to calculate a loss (first error). In the second learning (described later), the error calculation unit 164 compares the second recognition result output by the output layer 304 with the correct answer for the second data to calculate a loss (second error). The error calculation unit 164 then updates the weight parameters in the first input layer 301, the first intermediate layer 303, the first normalization layer 311, the second intermediate layer 313, and the output layer 304 from the layer on the output side toward the layer on the input side as illustrated in FIG. 5 (error backpropagation) so that the calculated loss decreases. Updating of these parameters is the first learning (step S106).

Second Learning

FIG. 6 is a diagram describing the second learning in the CNN 162. In FIG. 6, a downward arrow indicates that information is transmitted in a direction (learning direction) from the second input layer 302 to the output layer 304 via the first intermediate layer 303, the second normalization layer 312, and the second intermediate layer 313. An upward arrow opposite to the learning direction indicates that information is transmitted from the output layer 304 to the second input layer 302 via the second intermediate layers 313, the second normalization layer 312, and the first intermediate layer 303 (error backpropagation described later).

Second Feature Quantity Calculation Processing

In the second learning, a mini-batch is formed by a plurality of images (second data) selected from the plurality of special-light images recorded in the second image database 202, and the mini-batch is input to the second input layer 302. The second input layer 302 performs the second feature quantity calculation processing (step S107) to calculate the second feature quantity.

Second Intermediate Feature Quantity Calculation Processing

The first intermediate layer 303 receives the second feature quantity and performs the second intermediate feature quantity calculation processing to calculate the second intermediate feature quantity (step S108). Since the first input layer 301 and the second input layer 302 are connected to the first intermediate layer 303 as described above, the output of the first input layer 301 and the output of the second input layer 302 are input in a switching manner when learning is performed.

At the time of the second learning, the output is switched as illustrated in FIG. 6, so that the output from the second input layer 302 is input to the first intermediate layer 303. FIG. 7B is a diagram illustrating a state in which the second feature quantity is input to the first intermediate layer 303 (outputs from nodes 302A constituting the second input layer 302 are input to the nodes 303A constituting the first intermediate layer 303). In the state illustrated in FIG. 6, the second feature quantity based on the feature quantity output from the second input layer 302 is input to the first intermediate layer 303, and the second intermediate feature quantity is calculated in the first intermediate layer 303. FIG. 7B illustrates a state in which the second feature quantity is input to the first intermediate layer 303.

Similarly to FIG. 8A, FIG. 8B illustrates a state in which outputs of nodes X21, X22, and X23 of the second input layer 302 are respectively multiplied by weight parameters W21, W22, and W23 and the results are input to the node Y11 of the first intermediate layer 303 (in the state illustrated in FIG. 8B, the output is not input to the node Y11 from a node X20). FIG. 8B illustrates the input relationships between the nodes X21, X22, and X23 and the node Y11. The similar relationships are established also for other nodes Y10, Y12, and Y13 of the first intermediate layer 303.

Note that the "second normalized feature quantity calculation processing (step S109)", the "fourth intermediate feature quantity calculation processing (step S110)", the "second recognition result output processing (step S111)", and the "second learning (step S112)" in the second learning are substantially the same as the "first normalized feature quantity calculation processing (step S103)", the "third intermediate feature quantity calculation processing (step S104)", the "first recognition result output processing (step S105)", and the "first learning (step S106)" in the first learning, and thus description thereof is omitted.

Examples of Learning Patterns

The example in which each of the first learning and the second learning is performed once has been described in the description of the learning method presented above. However, the learning method performed by the learning apparatus 10 is not limited to this. It is sufficient that each of the first learning and the second learning is performed at least once, and various configurations may be adopted. An example of the number of times the processes are performed and the order in which the processes are performed will be described below.

FIRST EXAMPLE

In a first example, the second intermediate layer 313 outputs the fourth intermediate feature quantity in the second learning in a period after the third intermediate feature quantity in the preceding first learning is output and before the third intermediate feature quantity in the following first learning is output.

Figure 9A:
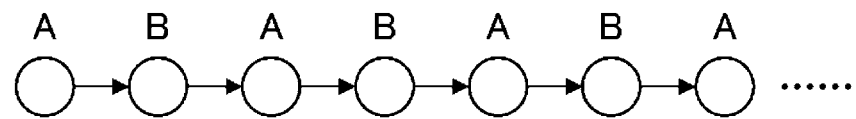
FIGS. 9A to 9C are diagrams illustrating patterns of the first learning and the second learning.

For example, the processing is repeated in an order illustrated in FIG. 9A. In FIG. 9A, "A" and "B" respectively represent "calculation of the third intermediate feature quantity in the second intermediate layer 313" and "calculation of the fourth intermediate feature quantity in the second intermediate layer 313", which are counted once, twice, and so on in units of mini-batches.

SECOND EXAMPLE

Figure 9B:
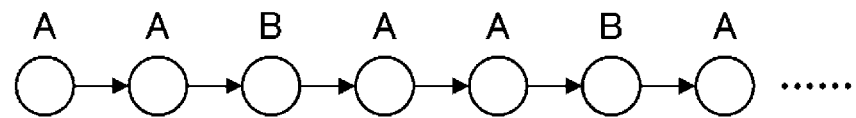
Figure 9C:
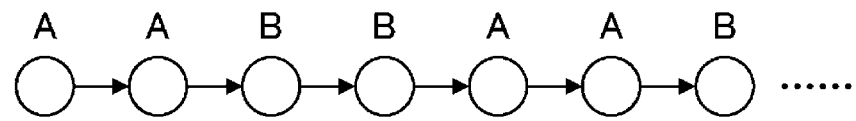

In a second example, the second intermediate layer 313 outputs the fourth intermediate feature quantity in the second learning after the output of the third intermediate feature quantity in the preceding first learning and the output of the third intermediate feature quantity in the following first learning are completed. For example, the processing is repeated in an order illustrated in FIG. 9B. "A" and "B" in FIG. 9B have the same meanings as those in FIG. 9A. In this case, "B" may be consecutively performed twice as illustrated in FIG. 9C.

THIRD EXAMPLE

Figure 10:
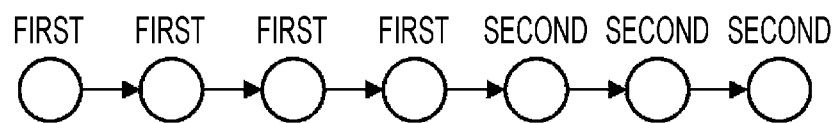
FIG. 10 is a diagram illustrating another pattern of the first learning and the second learning.

In a third example, the learning apparatus 10 consecutively performs the first learning a plurality of times and then consecutively performs the second learning a plurality of times. For example, the learning apparatus 10 performs learning in an order illustrated in FIG. 10. Note that "FIRST" and "SECOND" in FIG. 10 represent the "first learning" and the "second learning", respectively. Note that the patterns illustrated in FIGS. 9A to 10 are merely illustrative, and learning can be performed in various other patterns.

Advantages

In the learning apparatus 10, the first intermediate layer 303 outputs the first intermediate feature quantity when receiving the first feature quantity based on the first data and outputs the second intermediate feature quantity when receiving the second feature quantity based on the second data. The first normalization layer 311 receives the first intermediate feature quantity and outputs the first normalized feature quantity. The second normalization layer 312 receives the second intermediate feature quantity and outputs the second normalized feature quantity. The second intermediate layer 313 receives the first normalized feature quantity and the second normalized feature quantity. Thus, in this aspect, the first intermediate feature quantity derived from the first data and the second intermediate feature quantity derived from the second data can be normalized under different conditions. Thus, the first intermediate feature quantity and the second intermediate feature quantity can be appropriately normalized, and consequently the learning apparatus 10 can perform efficient learning.

In the learning apparatus 10, the first data and the second data are respectively input to the first input layer 301 and the second input layer 302 that are independent of each other, and a feature quantity is calculated in each of the first input layer 301 and the second input layer 302. Thus, the feature quantity calculation in one of the first and second input layers 301 and 302 is not affected by the feature quantity calculation in the other input layer. In the learning apparatus 10, in addition to feature extraction in the input layers (the first input layer 301 and the second input layer 302), the first intermediate feature quantity and the second intermediate feature quantity are further calculated in the first intermediate layer 303 common to the first input layer 301 and the second input layer 302. Thus, the feature quantity calculated from the first data or the second data in the input layer can be reflected in calculation of the intermediate feature quantity in the first intermediate layer 303. The second intermediate layer 313 is also common to the first normalization layer 311 and the second normalization layer 312. Thus, the first normalized feature quantity and the second normalized feature quantity can be similarly reflected in calculation of the intermediate feature quantity in the second intermediate layer 313. In addition, since a hierarchical network involves many parameters, overlearning is likely to occur. However, overlearning can be avoided by providing a large amount of data. In the learning apparatus 10, since learning can be performed in the intermediate layer using a large amount of data including both the first data and the second data, overlearning is unlikely to occur. On the other hand, since the input layer is implemented as the first input layer 301 and the second input layer 302 that are independent of each other, the number of parameters of each input layer reduces. Thus, overlearning is unlikely to occur even with a small amount of data.

The learning apparatus 10 can appropriately learn pieces of data that belong to the same category but are acquired under different conditions in this manner.

Learning Using Combined Mini-Batch

In the learning patterns described above, the feature quantities are calculated separately for the first data and the second data in units of mini-batches. Alternatively, a first mini-batch and a second mini-batch may be combined into a single mini-batch immediately before the mini-batch is input to the first intermediate layer 303. Specifically, a mini-batch (first mini-batch) is formed by a plurality of images (first data) selected from the plurality of normal-light images recorded in the first image database 201, and the mini-batch is input to the first input layer 301 to calculate a feature quantity. In addition, a mini-batch (second mini-batch) is formed by a plurality of images (second data) selected from the plurality of special-light images recorded in the second image database 202, and the mini-batch is input to the second input layer 302 to calculate a feature quantity. The first mini-batch and the second mini-batch may be combined for these feature quantities into a single mini-batch immediately before the input to the first intermediate layer 303, and the combined mini-batch may be input to the first intermediate layer 303.

Recognition Processing

As the learning described above (the first learning and the second learning) progresses, the CNN 162 of the recognizer 100 becomes a trained model. In the recognition (inference) processing using the CNN 162 which has become the trained model, recognition may be performed with a configuration in which either the first input layer 301 or the second input layer 302 is disconnected. For example, the recognition can be performed for the first data in a state in which the second input layer 302 is disconnected and the first input layer 301 alone is connected as illustrated in FIG. 5. In addition, the recognition can be performed for the second data in a state in which the first input layer 301 is disconnected and the second input layer 302 alone is connected as illustrated in FIG. 6.

Learning Using First Narrow-Band-Light Images and Second Narrow-Band-Light Images In the example described above, learning using normal-light images (white-light images) and special-light images (for example, blue special-light images) has been described. However, learning may be performed using a plurality of narrow-band-light images for which wavelength balances of the observation light are different. The first input layer 301 may receive, as first image data, first medical image data acquired using first narrow-band light as first observation light. The second input layer 302 may receive, as second image data, second medical image data acquired using, as second observation light, second narrow-band light different from the first narrow-band light. In this case, as the narrow-band light combination, blue light in a plurality of narrow bands, a combination of blue light in a narrow band and violet light in a narrow band, red light in a plurality of narrow bands, or the like can be used.

Learning Using Other Data

In the embodiment described above, learning using endoscopic images acquired using different kinds of observation light has been described. However, with the learning apparatus and the learning method according to the present invention, learning can be performed likewise in the case where medical images other than the endoscopic images, such as images acquired by a computed tomography (CT) apparatus, a magnetic resonance imaging (MRI) apparatus, or the like, are used. In addition, learning can be performed likewise even in the case where images other than medical images (other images of, for example, persons, animals, or sceneries) are used. Further, learning can be performed likewise also in the case where the input data is not of images but is of text, sound, or the like.

Although examples of the present invention have been described above, the present invention is not limited to the above-described embodiments, and it is needless to say that various modifications can be made within a scope not departing from the gist of the present invention.

REFERENCE SIGNS LIST

10 learning apparatus
100 recognizer
110 image acquisition unit
120 operation unit
130 control unit
140 display unit
142 monitor
150 recording unit
160 processing unit
164 error calculation unit
201 first image database
202 second image database
301 first input layer
302 second input layer
303 first intermediate layer
304 output layer
311 first normalization layer
312 second normalization layer
313 second intermediate layer

What is claimed is:

1. A learning apparatus comprising: a processor configured to implement:
   a to-be-trained model of a recognizer; and
   a learning control unit that trains the to-be-trained model, wherein
   the to-be-trained model comprises a hierarchical network including
      a first input layer that receives first data and outputs a first feature quantity, the first data being data selected from a first data group constituted by a plurality of pieces of data acquired under a first condition,
      a second input layer that is independent of the first input layer and that receives second data and outputs a second feature quantity, the second data being data selected from a second data group constituted by a plurality of pieces of data that belong to a category identical to a category of the pieces of data constituting the first data group and that are acquired under a second condition different from the first condition,
      a first intermediate layer that is an intermediate layer common to the first input layer and the second input layer and that outputs a first intermediate feature quantity in response to receiving the first feature quantity and outputs a second intermediate feature quantity in response to receiving the second feature quantity,
      a first normalization layer that receives the first intermediate feature quantity and outputs a first normalized feature quantity based on the first intermediate feature quantity,
      a second normalization layer that receives the second intermediate feature quantity and outputs a second normalized feature quantity based on the second intermediate feature quantity,
      a second intermediate layer that is an intermediate layer common to the first normalization layer and the second normalization layer and that outputs a third intermediate feature quantity in response to receiving the first normalized feature quantity and outputs a fourth intermediate feature quantity in response to receiving the second normalized feature quantity, and
      an output layer that receives the third intermediate feature quantity or the fourth intermediate feature quantity and outputs a first recognition result based on the third intermediate feature quantity in response to receiving the third intermediate feature quantity and outputs a second recognition result based on the fourth intermediate feature quantity in response to receiving the fourth intermediate feature quantity, and
   the learning control unit causes first learning and second learning to be performed, the first learning being learning in which the to-be-trained model is trained based on a first error between the first recognition result and a correct answer for the first data, the second learning being learning in which the to-be-trained model is trained based on a second error between the second recognition result and a correct answer for the second data.

2. The learning apparatus according to claim 1, wherein the learning control unit causes the first learning to be performed at least twice, and
   the second intermediate layer outputs the fourth intermediate feature quantity in the second learning in a period after the third intermediate feature quantity in the preceding first learning is output and before the third intermediate feature quantity in the following first learning is output.

3. The learning apparatus according to claim 1, wherein the learning control unit causes the first learning to be performed at least twice, and
   the second intermediate layer outputs the fourth intermediate feature quantity in the second learning after output of the third intermediate feature quantity in the preceding first learning and output of the third intermediate feature quantity in the following first learning are completed.

4. The learning apparatus according to claim 1, wherein the hierarchical network is a convolutional neural network.

5. The learning apparatus according to claim 1, wherein the first normalization layer calculates the first normalized feature quantity through a batch normalization process, and the second normalization layer calculates the second normalized feature quantity through a batch normalization process.

6. The learning apparatus according to claim 1, wherein the first input layer outputs the first feature quantity through an operation including any one of a convolutional operation, a pooling process, a batch normalization process, or an activation process.

7. The learning apparatus according to claim 1, wherein the second input layer outputs the second feature quantity through an operation including any one of a convolutional operation, a pooling process, a batch normalization process, or an activation process.

8. The learning apparatus according to claim 1, wherein the first intermediate layer outputs the first intermediate feature quantity or the second intermediate feature quantity through an operation including any one of a convolutional operation, a pooling process, or an activation process.

9. The learning apparatus according to claim 1, wherein the second intermediate layer outputs the third intermediate feature quantity or the fourth intermediate feature quantity through an operation including any one of a convolutional operation, a pooling process, or an activation process.

10. The learning apparatus according to claim 1, wherein
the first input layer receives, as the first data, first image data acquired under the first condition, and
the second input layer receives, as the second data, second image data acquired under the second condition different from the first condition.

11. The learning apparatus according to claim 10, wherein the first condition and the second condition are different from each other in at least one of an imaging device, a wavelength balance of observation light, a resolution, or image processing to be performed on an image.

12. The learning apparatus according to claim 11, wherein
the first input layer receives, as the first image data, first medical image data acquired using first observation light, and
the second input layer receives, as the second image data, second medical image data acquired using second observation light different from the first observation light in the wavelength balance.

13. The learning apparatus according to claim 12, wherein
the first input layer receives, as the first image data, the first medical image data acquired using white light as the first observation light, and
the second input layer receives, as the second image data, the second medical image data acquired using narrow-band light as the second observation light.

14. The learning apparatus according to claim 12, wherein
the first input layer receives, as the first image data, the first medical image data acquired using first narrow-band light as the first observation light, and
the second input layer receives, as the second image data, the second medical image data acquired using, as the second observation light, second narrow-band light different from the first narrow-band light.

15. A learning method for a learning apparatus comprising a processor configured to implement a to-be-trained model of a recognizer, and a learning control unit that trains the to-be-trained model,
the to-be-trained model comprising a hierarchical network including
a first input layer that receives first data and outputs a first feature quantity, the first data being data selected from a first data group constituted by a plurality of pieces of data acquired under a first condition,
a second input layer that is independent of the first input layer and that receives second data and outputs a second feature quantity, the second data being data selected from a second data group constituted by a plurality of pieces of data that belong to a category identical to a category of the pieces of data constituting the first data group and that are acquired under a second condition different from the first condition,
a first intermediate layer that is an intermediate layer common to the first input layer and the second input layer and that outputs a first intermediate feature quantity in response to receiving the first feature quantity and outputs a second intermediate feature quantity in response to receiving the second feature quantity,
a first normalization layer that receives the first intermediate feature quantity and outputs a first normalized feature quantity based on the first intermediate feature quantity, a second normalization layer that receives the second intermediate feature quantity and outputs a second normalized feature quantity based on the second intermediate feature quantity,
a second intermediate layer that is an intermediate layer common to the first normalization layer and the second normalization layer and that outputs a third intermediate feature quantity in response to receiving the first normalized feature quantity and outputs a fourth intermediate feature quantity in response to receiving the second normalized feature quantity, and
an output layer that receives the third intermediate feature quantity or the fourth intermediate feature quantity and outputs a first recognition result based on the third intermediate feature quantity in response to receiving the third intermediate feature quantity and outputs a second recognition result based on the fourth intermediate feature quantity in response to receiving the fourth intermediate feature quantity,
the learning method comprising:
a first learning step of training, with the learning control unit, the to-be-trained model on the basis of a first error between the first recognition result and a correct answer for the first data; and
a second learning step of training, with the learning control unit, the to-be-trained model on the basis of a second error between the second recognition result and a correct answer for the second data.

16. A non-transitory, computer-readable tangible recording medium which records thereon a program for causing, when read by a computer, a processor of the computer to execute the learning method according to claim 15.

17. A trained model of a recognizer obtained through the learning method according to claim 15.

18. An endoscope system comprising the trained model of the recognizer according to claim 17.

19. The endoscope system according to claim 18, wherein the first condition and the second condition are different from each other in at least one of an imaging device, a wavelength balance of observation light, a resolution, or image processing to be performed on an image.

* * * * *